United States Patent

Wyman et al.

[11] Patent Number: 5,952,325
[45] Date of Patent: Sep. 14, 1999

[54] TRICYCLIC SPIRO COMPOUNDS PROCESS FOR THEIR PREPARATION AND THEIR USE OF 5HT1D RECEPTOR ANTAGONISTS

[75] Inventors: Paul Adrian Wyman, Epping; Laramie Mary Gaster, Bishop's Stortford; Andrew John Jennings, Hertford, all of United Kingdom

[73] Assignee: SmithKline Beecham plc, Brentford, United Kingdom

[21] Appl. No.: 08/817,619

[22] PCT Filed: Oct. 5, 1995

[86] PCT No.: PCT/EP95/03945

§ 371 Date: Apr. 16, 1997

§ 102(e) Date: Apr. 16, 1997

[87] PCT Pub. No.: WO96/11934

PCT Pub. Date: Apr. 25, 1996

[30] Foreign Application Priority Data

Oct. 18, 1994 [GB] United Kingdom .................... 9421003

[51] Int. Cl.$^6$ .................... C07D 491/107; C07D 495/10; A61K 31/435; A61K 31/55
[52] U.S. Cl. ................. 514/212; 514/278; 514/409; 540/543; 546/16; 546/17; 548/409
[58] Field of Search ................ 546/16, 17; 540/543; 548/409; 514/278, 409, 212

[56] References Cited

U.S. PATENT DOCUMENTS

| | | | |
|---|---|---|---|
| 5,756,496 | 5/1998 | Ham et al. | 514/211 |
| 5,817,833 | 10/1998 | Gaster | 548/484 |

OTHER PUBLICATIONS

J. W. Clitherow et al., *Journal of Medicinal Chemistry*, vol. 37, No. 15, pp. 2253–2257 (1994).

*Primary Examiner*—Alan L. Rotman
*Attorney, Agent, or Firm*—Wayne J. Dustman; William T. King; Charles M. Kinzig

[57] ABSTRACT

Novel amide derivatives of formula (I), processes for their preparation, pharmaceutical compositions containing them and their use as medicaments are disclosed.

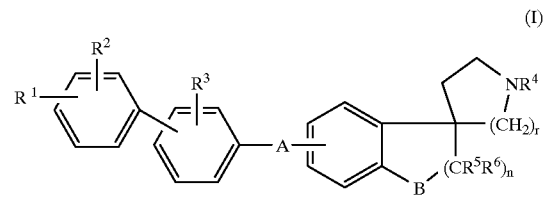

8 Claims, No Drawings

TRICYCLIC SPIRO COMPOUNDS PROCESS FOR THEIR PREPARATION AND THEIR USE OF 5HT1D RECEPTOR ANTAGONISTS

CROSS-REFERENCE

This application is a 371 of PCT/EP95/03945 filed Oct. 5,1995.

The present invention relates to novel amide derivatives, processes for their preparation, and pharmaceutical compositions containing them.

EPA 0 533 266/7/8 disclose a series of benzanilide derivatives which are said to possess $5HT_{1D}$ receptor antagonist activity. These compounds are said to be of use in the treatment of various CNS disorders.

A structurally distinct class of compounds have now been discovered and have been found to exhibit $5HT_{1D}$ antagonist activity. In a first aspect, the present invention therefore provides a compound of formula (I) or a salt thereof:

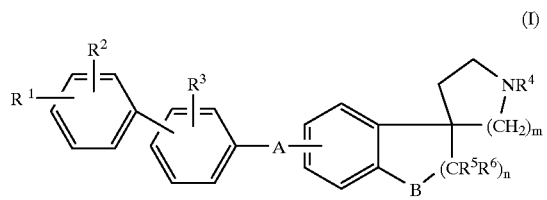

in which

R$^1$ is NR$^9$CONR$^{10}$R$^{11}$, NR$^{10}$SO$_2$R$^{11}$, SO$_2$NR$^{10}$R$^{11}$, CO$_2$R$^{10}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, NR$^{10}$R$^{11}$, NR$^{10}$CO$_2$R$^{11}$, CONHNR$^{10}$R$^{11}$, CR10=NOR$^{11}$, CNR$^{10}$=NOR$^{11}$, where R$^9$, R$^{10}$ and R$^{11}$ are independently hydrogen or C$_{1-6}$alkyl and a is 1 to 4; or R$^1$ is an optionally substituted 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl;

R$^4$ is hydrogen or C$_{1-6}$alkyl;

R$^5$ and R$^6$ are independently hydrogen or C$_{1-6}$alkyl;

A is CONH;

B is oxygen, sulphur, CR$^{12}$R$^{13}$ or NR$^{14}$ where R$^{12}$, R$^{13}$ and R$^{14}$ are independently hydrogen or C$_{1-6}$alkyl;

m is 1, 2 or 3; and n is 1, 2 or 3.

C$_{1-6}$alkyl groups, whether alone or as part of another groups may be straight chain or branched.

Suitably R$^1$ is NR$^9$CONR$^{10}$R$^{11}$, NR$^{10}$SO$_2$R$^{11}$, SO$_2$NR$^{10}$R$^{11}$, CO$_2$R$^{10}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, NR$^{10}$R$^{11}$, NR$^{10}$CO$_2$R$^{11}$, CONHNR$^{10}$R$^{11}$, CR10=NOR$^{11}$, CNR$^{10}$=NOR$^{11}$, where R$^9$, R$^{10}$ and R$^{11}$ are independently hydrogen or C$_{1-6}$alkyl and a is 1 to 4 or R$^1$ is an optionally substituted 5 to 7-membered heterocyclic ring containing 1 to 4 selected from oxygen, nitrogen or sulphur.

When R$^1$ is a 5 to 7-membered heterocyclic ring containing 1 to 3 heteroatoms selected from oxygen, nitrogen or sulphur suitable heterocyclic rings include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Suitable substituents for these rings include R$^2$ and R$^3$ groups as defined above. Preferably R$^1$ is optionally substituted oxadiazolyl. Preferred substituents for such oxadiazolyl groups include C$_{1-6}$alkyl such as methyl or ethyl. Most preferably R$^1$ is a 5-methyl-1,2,4-oxadiazol-3-yl group.

Suitably R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxy C$_{1-6}$alkyl, C$_{1-6}$alkylOC$_{1-6}$alkyl, acyloxy, hydroxy, nitro, trifluoromethyl, cyano, CO$_2$R$^9$, CONR$^{10}$R$^{11}$, NR$^{10}$R$^{11}$ where R$^9$, R$^{10}$ and R$^{11}$ are independently hydrogen or C$_{1-6}$alkyl. Preferably R$^1$ and R$^2$ are C$_{1-6}$alkyl, in particular methyl. Preferably R$^3$ is hydrogen.

Suitably R$^4$ is hydrogen or C$_{1-6}$alkyl. Preferably R$^4$ is methyl.

Suitably R$^5$ and R$^6$ are independently hydrogen or C$_{1-6}$alkyl. Preferably R$^5$ and R$^6$ are both hydrogen.

Suitably B is oxygen, sulphur, CR$^{12}$R$^{13}$ or NR$^{14}$ where R$^{12}$, R$^{13}$ and R$^{14}$ are independently hydrogen or C$_{1-6}$alkyl. Preferably B is oxygen.

Suitably m is 1, 2 or 3, preferably m is 2.

Suitably n is 1 or 2, preferably n is 1.

Particularly preferred compounds of the invention include:

N-(2,3-Dihydro-1'-methylspiro[4H-benzopyran-6-yl-4,4'-piperidine])-2'-methyl-4'-(5-methyl-1,2,4-oxadiazol-3-yl)biphenyl-4-carboxamide, N-(2,3-Dihydrospiro[4H-benzopyran-6-yl-4,4'-piperidine])-2'-methyl-4'-(5-methyl-1,2,4-oxadiazol-3-yl)biphenyl-4-carboxamide, N-(2,3-Dihydro-1'-methylspiro[benzofuran-5-yl-3,4'-piperidine])-2'-methyl-4'-(5-methyl-1,2,4-oxadiazol-3-yl)biphenyl-4-carboxamide, N-(2,3-Dihydro-1'-methylspiro[benzothiophen-5-yl-3,4'-piperidine])-2'-methyl-4'-(5-methyl-1,2,4-oxadiazol-5-yl)biphenyl-4-carboxamide, N-(1,2,3,5,6,7-Hexahydro-1-methylspiro[4H-azepine-4,3'(2H)-benzofuran-5'-yl])-2'-methyl-4'-(5-methyl-1,2,4-oxadiazol-3-yl)biphenyl-4-carboxamide, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises.

(a) reaction of a compound of formula (II):

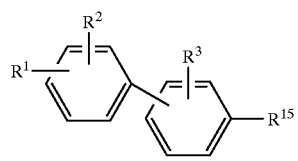

with a compound of formula (III):

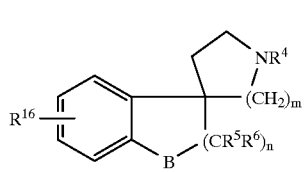

wherein $R^1$, $R^2$, $R^3$, $R^4$, $R^5$, $R^6$, B, m and n are as defined in formula (I) and $R^{15}$ and $R^{16}$ contain the appropriate functional group(s) necessary to form the A moiety; and optionally thereafter in any order:
converting a compound of formula (I) into another compound of formula (I)
forming a pharmaceutically acceptable salt.

Suitably $R^{15}$ is an activated carboxylic acid derivative, such as an acyl halide or acid anhydride, and $R^{16}$ is an amine group. Activated compounds of formulae (II) or (III) can also be prepared by reaction of the corresponding carboxylic acid with a coupling reagent such as carbonyldiimidazole, dicyclohexylcarbodiimide or diphenylphosphorylazole. Preferably $R^{15}$ or is a group COL where L is halo, particularly chloro.

A compound of formulae (II) and (III) are typically reacted together in an inert organic solvent such as DMF, THF or dichloromethane at ambient or elevated temperature in the presence of a base such as an alkali metal hydroxide, triethylamine or pyridine.

Intermediate compounds of formulae (II) and (III) are commercially available or can be prepared using standard procedures such as those outlined in EPA 533266/7/8. Certain intermediate compounds of formulae (II) and (III) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

4-(2-(2-Iodophenoxy)ethyl)pyridine

A stirred solution of 2-iodophenol (8.8 g, 0.040 mole), triphenylphosphine (10.5 g, 0.040 mole) and pyridine-4-ethanol (5.5 g, 0.045 mole) in THF (200 ml) at 0° C. under argon was treated with a solution of diethyl azodicarboxylate (6.3 ml, 0.040 mole) in THF (30 ml). The solution was allowed to warm to room temp. and stirred for 4 h, then concentrated in vacuo and the residue treated with 10% $Na_2CO_3$ solution (80 ml) and extracted with ethyl acetate (2×80 ml). The combined organic was extracted with 1M HCl acid (150 ml), then the acid extract basified by addition of potassium carbonate and extracted with ethyl acetate (2×100 ml). The combined extract was dried ($Na_2SO_4$) and concentrated in vacuo to leave a brown oil, which was chromatographed on silica gel eluting with 0 to 15% ethyl acetate/ether to afford the title compound as a colourless oil (9.3 g, 72%).

$^1$H NMR (250 MHz, $CDCl_3$)

δ(ppm): 8.58–8.51 (m, 2H), 7.76 (dd, 1H), 7.40–7.22 (m, 3H), 6.82–6.68 (m, 2H), 4.23 (t, 2H), 3.15 (t, 2H).

DESCRIPTION 2

4-(2-(2-Iodophenoxy)ethyl)-1-methyl-1,2,3,6-tetrahydropyridine

A solution of 4-(2-(2-iodophenoxy)ethyl)pyridine (D1, 8.28 g, 0.025 mole) in acetone (220 ml) was treated with iodomethane (3.7 ml, 0.059 mole) and kept at room temperature for 24 h, then concentrated in vacuo to leave the quaternary salt as a yellow oil. This was dissolved in a mixture of ethanol (50 ml) and water (50 ml), cooled to 0° C. under argon and treated portionwise over 1 h with sodium borohydride (1.33 g, 0.035 mole). The reaction mixture was kept at 0° C. for a further 1 h, then treated with 10% NaOH solution (50 ml), diluted with water (120 ml) and extracted with ethyl acetate (2×200 ml). The combined extract was dried ($Na_2SO_4$), concentrated in vacuo to leave an orange oil, which was chromatographed on silica gel eluting with 0 to 10% methanol/chloroform to afford the title compound as a yellow oil (6.19 g, 72%)

$^1$H NMR (250 MHz, $CDCl_3$)

δ(ppm): 7.76 (dd, 1H), 7.28 (dt, 1H), 6.79 (dd, 1H), 6.70 (dt, 1H), 5.57 (m, 1H), 4.09 (t, 2H), 3.00–2.90 (m, 2H), 2.65–2.48 (m, 4H), 2.36 (s, 3H), 2.32–2.20 (m, 2H).

DESCRIPTION 3

2,3-Dihydro-1'-methylspiro[4H-benzopyran-4,4'-piperidine]

A stirred solution of 4-(2-(2-iodophenoxy)ethyl)-1-methyl-1,2,3,6tetrahydropyridine (D2, 6.3 g, 0.018 mole) and AIBN (50 mg) in benzene (700 ml) was heated to-reflux under argon, then treated dropwise over 1 h with a solution of tributyltin hydride (9.7 ml, 0.036 mole) in benzene (100 ml). The reaction mixture was heated under reflux for a further 3 h after completing the addition, then more tributyltin hydride (3.8 ml, 0.014 mole) and AIBN (30 mg) were added and heating under reflux was continued for 4 h. The reaction mixture was allowed to cool, then concentrated in vacuo and the residue treated with 2M HCl acid (150 ml), washed with ethyl acetate (100 ml), basified with potassium carbonate and extracted with ethyl acetate (2×100 ml). The combined extract was dried ($Na_2SO_4$) and concentrated in vacuo to leave a yellow oil, which was chromatographed on silica gel eluting with 0 to 2% methanol/chloroform to afford the title compound (2.3 g of approx. 86% purity, 51%).

$^1$H NMR (250 MHz, $CDCl_3$)

δ(ppm): 7.38 (dd, 1H), 7.08 (dt, 1H), 6.90 (dt, 1H), 6.79 (dd, 1H), 4.18–4.10 (m, 2H), 2.83–2.70 (m, 2H), 2.45–2.25 (m, 4H), 2.35 (s, 3H), 2.05–1.95 (m, 2H), 1.70–1.55 (m, 2H).

DESCRIPTION 4

2,3-Dihydro-1'-ethoxycarbonylspiro[4H-benzopyran-4,4'-piperidine]

A stirred solution of 2,3-dihydro-1'-methylspiro[4H-benzopyran-4,4'-piperidine] (D3, 1.0 g, 0.0046 mole) and diisopropylethylamine (1.2 ml, 0.0070 mole) in dichloroethane (20 ml) was treated with 1-chloroethyl chloroformate (0.64 ml, 0.0060 mole) and kept at room temp. for 1 h followed by 20 mins at reflux. The solution was then concentrated in vacuo and the residue treated with methanol (20 ml) and heated under reflux for 2 h. The reaction mixture was concentrated in vacuo to leave a beige solid, which was dissolved in dichloromethane (50 ml) and THF (10 ml) and treated with triethylamine (0.84 ml, 0.0060 mole) followed by ethyl chloroformate (0.44 ml, 0.0046 mole). The solution was stirred at room temperature for 2 h, then treated with 10% $Na_2CO_3$ solution (20 ml) and extracted with dichloromethane (2×40 ml). The combined extract was dried ($Na_2SO_4$) and concentrated in vacuo. The residue was chromatographed on silica gel eluting with 1:1 ether/60–80 petrol to afford the title compound as a yellow oil (1.3 g, 100%).

$^1$H NMR (250 MHz, $CDCl_3$)

δ(ppm): 7.25 (dd, 1H), 7.10 (dt, 1H), 6.90 (dt, 1H), 6.80 (dd, 1H), 4.25–4.00 (m, 6H), 2.98 (br t, 2H), 2.10–1.92 (m, 4H), 1.70–1.53 (m, 2H), 1.28 (t, 3H).

DESCRIPTION 5

2,3-Dihydro-1'-ethoxycarbonyl-6- and 8-nitrospiro [4H-benzopyran-4,4'piperidine]

A stirred solution of 2,3-dihydro-1'-ethoxycarbonylspiro [4H-benzopyran-4,4'-piperidine] (D4, 1.3 g, 0.0046 mole) in acetic anhydride (30 ml) at 0° C. under argon was treated portionwise over 15 minutes with copper (II) nitrate hemipentahydrate (1.16 g, 0.0050 mole). The reaction mixture was kept at 0° C. for a total of 1.5 h, then allowed to warm to room temperature over 0.5 h. The mixture was poured into water/ice (300 ml) and basified by careful addition of potassium carbonate, then extracted with ethyl acetate (×100 ml). The combined extract was dried ($Na_2SO_4$) and concentrated in vacuo to afford an orange oil (1.5 g, 100%), which was approximately a 1:1 mixture of 6- and 8-nitro isomers. This was used without purification.

$^1$H NMR (250 MHz, $CDCl_3$)

δ(ppm): 8.24 (d, 1H 6-isomer), 8.00 (dd, 1H 6-isomer), 7.64 (dd, 1H 8-isomer), 7.52 (dd, 1H 8-isomer), 6.98 (t, 1H 8-isomer), 6.90 (d, 1H 6-isomer), 4.35–4.05 (m, 6H), 3.00 (br t, 2H), 2.25–1.95 (m, 4H), 1.75–1.60 (m, 2H), 1.35–1.22 (m, 3H).

DESCRIPTION 6

6-Amino-2,3-dihydro-1'-ethoxycarbonylspiro[4H-benzopyran-4,4'-piperidine]

A solution of 2,3-dihydro-1'-ethoxycarbonyl-6- and 8-nitrospiro[4H-benzopyran-4,4'-piperidine] (D5, 1.5 g, 0.0046 mole) in ethanol (100 ml) was hydrogenated over 10% Pd-C (300 mg) at atmospheric temperature and pressure until uptake of hydrogen ceased. The catalyst was removed by filtration through kieselguhr and the filtrate concentrated in vacuo. The mixture of 6- and 8-amino isomers was separated by chromatography on silica gel eluting with ether to afford the 6-amino compound as the lower rf component (420 mg, 32%).

$^1$H NMR (250 MHz, $CDCl_3$)

δ(ppm): 6.66 (d, 1H), 6.60 (d, 1H), 6.50 (dd, 1H), 4.25–4.00 (m, 4H), 4.17 (q, 2H), 3.45 (br s, 2H), 2.98 (br t, 2H), 2.08–1.88 (m, 4H), 1.70–1.55 (m, 2H), 1.30 (t, 3H).

DESCRIPTION 7

6-Amino-2,3-dihydro-1'-methylspiro[4H-benzopyran-4,4'-piperidine]

A stirred suspension of lithium aluminium hydride (76 mg, 0.0020 mole) in THF (15 ml) at 0° C. under argon was treated with a solution of 6-amino-2,3-dihydro-1'-ethoxycarbonylspiro[4H-benzopyran-4,4'-piperidine] (D6, 300 mg, 0.0010 mole) in THF (5 ml). The reaction mixture was allowed to warm to room temp. and stir for 1.5 h, then treated with more lithium aluminium hydride (38 mg, 0.0010 mole) suspended in THF (5 ml). The mixture was heated under reflux for 0.75 h, then cooled in an ice bath and treated with water (0.10 ml), 10% NaOH solution (0.10 ml) and water (0.30 ml). The resulting mixture was filtered through kieselguhr and the filtrate concentrated in vacuo to afford the title compound as a yellow oil (200 mg, 84%).

$^1$H NMR (200 MHz, $CDCl_3$)

δ(ppm): 6.73 (d, 1H), 6.65 (d, 1H), 6.48 (dd, 1H), 4.10–4.00 (m, 2H), 3.3 (brs, 2H), 2.85–2.70 (m, 2H), 2.35 (s, 3H), 2.30–1.90 (m, 6H), 1.75–1.53 (m, 2H).

DESCRIPTION 8

N-(2,3-Dihydro-1'-ethoxycarbonylspiro[4H-benzopyran-6-yl-4,4'-piperidine])-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 6-amino-2,3-dihydro-1'-ethoxycarbonylspiro[4H-benzopyran-4,4'-piperidine] (D6) using a similar procedure to Example 1 and purified by column chromatography on silica gel eluting with 1:1 ethyl acetate/60–80 petrol (87%).

$^1$H NMR (200 MHz, $CDCl_3$)

δ(ppm): 8.05–7.90 (m, 5H), 7.69 (d, 1H), 7.45 (d, 2H), 7.39–7.28 (m, 2H), 6.83 (d, 1H), 4.25–4.05 (m, 6H), 3.00 (br t, 2H), 2.69 (s, 3H), 2.35 (s, 3H), 2.15–1.95 (m, 4H), 1.78–1.57 (m, 2H), 1.29 (t, 3H).

DESCRIPTION 9

4-(Hydroxymethyl)-1-methyl-1,2,3,6-tetrahydropyridine

To a solution of ethyl 1-methyl-1,2,3,6tetrahydro-4-pyridinecarboxylate (10.0 ml, 0.061 mole) in THF (200 ml) was added, maintaining temperature below 25° C., lithium aluminium hydride (2.76 g, 0.073 mole). After stirring for a further 15 min, water (2.75 ml), 10% NaOH (4 ml) and water (4 ml) were successively added, and the mixture was filtered. The filtrate was dried ($Na_2SO_4$) and evaporated in vacuo to give the title compound as an amber oil (6.30 g, 81%), which solidified on standing.

$^1$H NMR (200 MHz, $CDCl_3$)

δ(ppm): 5.63 (m, 1H), 4.01 (s, 2H), 2.94 (m, 2H), 2.55 (t, 2H), 2.35 (s, 3H), 2.20 (m, 2H).

DESCRIPTION 10

4-(2-Iodophenoxymethyl)-1-methyl-1,2,3,6-tetrahydropyridine

The title compound was prepared from 4-(hydroxymethyl)-1-methyl-1,2,3,6-tetrahydropyridine (D9) and 2-iodophenol, using a procedure similar to that of Description 1 in 74% yield.

$^1$H NMR (200 MHz, $CDCl_3$)

δ(ppm): 7.76 (dd, 1H), 7.27 (m, 1H), 6.81 (dd, 1H), 6.68 (td, 1H), 5.84 (m, 1H), 4.47 (s, 2H), 2.99 (m, 2H), 2.58 (t, 2H), 2.4–2.25 (m, 5H).

DESCRIPTION 11

2,3-Dihydro-1'-methylspiro[benzofuran-3,4'-piperidine]

The title compound was prepared from 4-(2-iodophenoxymethyl)-1-methyl-1,2,3,6-tetrahydropyridine (D10), using a procedure similar to that of Description 3, in 69% yield.

$^1$H NMR (250 MHz, $CDCl_3$)

δ(ppm): 7.15 (m, 2H), 6.88 (t, 1H), 6.79 (d, 1H), 4.35 (s, 2H), 2.87 (m, 2H), 2.33 (s, 3H), 2.02 (m, 4H), 1.78 (m, 2H).

DESCRIPTION 12

2,3-Dihydro-1'-methyl-5-nitrospiro[benzofuran-3,4'-piperidine]

The tide compound was prepared from 2,3-dihydro-1'-methylspiro[benzofuran-3,4'-piperidine] (D11), using a procedure similar to that of Description 5, in 79% yield. The product was contaminated (NMR) by a minor amount of the 7-nitro isomer (ratio ca. 5:1).

$^1$H NMR (200 MHz, $CDCl_3$)

δ(ppm): 8.11 (dd, 1H), 8.03 (d, 1H), 6.83 (d, 1H), 4.53 (s, 2H), 2.91 (m, 2H), 2.34 (s, 3H), 2.02 (m, 4H), 1.81 (m, 2H).

DESCRIPTION 13

5-Amino-2,3-dihydro-1'-methylspiro[benzofuran-3,4'-piperidine]

The title compound was prepared from 2,3-dihydro-1'-methyl-5-nitrospiro[benzofuran-3,4'-piperidine] (D12), using a procedure similar to that of Description 6, in 60% yield.

$^1$H NMR (250 MHz, d$^6$DMSO)

δ(ppm): 6.42 (m, 2H), 6.33 (dd, 1H), 4.22 (s, 2H), 2.84 (d, 2H), 2.29 (s, 3H), 2.12 (t, 2H), 1.82 (td, 2H), 1.61 (d, 2H).

DESCRIPTION 14

4-[(2-Bromo-4-nitrophenylthio)mhethyl]pyridine

To a stirred solution of 2-bromo-4-nitrothiophenol (2.22 g, 9.5 mmol) (G.B. patent 1,122,323 C.A. 69, 106566) in dry DMF (20 ml) under argon was added anhydrous potassium carbonate (3.27 g, 23.7 mmol), followed by 4-picolyl chloride hydrochloride (1.56 g, 9.49 mmol). After 16 h, the mixture was poured into water (100 ml). The resultant suspension was extracted with ethyl acetate (2×60 ml). The combined organic layers were washed with water (3×60 ml), dried (Na$_2$SO$_4$) and evaporated under reduced pressure to give an orange oil, which was purified by silica gel chromatography (EtOAc as eluant) to give the title compound (1.55 g, 53%) as an orange solid.

$^1$H NMR (250 MHz, CDCl$_3$) δ (ppm): 8.62 (d, 2H), 8.40 (d, 1H), 8.08 (dd, 1H), 7.38 (d, 2H), 7.18 (d, 1H), 4.20 (s, 2H).

DESCRIPTION 15

4-[(4-Amino-2-bromophenylthio)methyl]pyridine

4-[(2-Bromo-4-nitrophenylthio)methyl]pyridine (D14) (0.800 g, 2.56 mmol) was dissolved in ethanol (40 ml) and heated to 60° C. with stifling. A solution of tin (II) chloride (1.696 g, 8.96 mmol) in conc. HCl (8 ml) was then added dropwise. The reaction mixture was heated under reflux for 2 h, then allowed to cool, diluted with water (40 ml) and basified to pH14 by the addition of 10% sodium hydroxide. The reaction mixture was concentrated in vacuo and the aqueous residue was extracted with dichloromethane (2×70 ml). The combined organic layers were then dried (Na$_2$SO$_4$) and evaporated under reduced pressure to give the title compound as a brown oil, which was dried in vacuo (0.670 g, 93%).

$^1$H NMR (250 MHz, CDCl$_3$) δ (ppm): 8.48 (d, 2H), 7.08 (d, 2H), 7.00 (d, 1H), 6.92 (d, 1H), 6.42 (dd, 1H), 3.90 (s, 2H), 3.80 (s, 2H).

DESCRIPTION 16

N-[3-Bromo-4-(pyrid-4.ylmethylthio)phenyl]-2'-methyl-4'-(5-methyl-1,2,4-oxadiazol-3-yl)biphenyl-4-carboxamide 2'-Methyl-4'-(5-methyl-1,2,4-oxadiazol-3-yl)biphenyl-4-carboxylic acid (EP 0533267A1) (0.895 g, 3.05 mmol) was suspended in dichloromethane (50 ml) with stirring. Oxalyl chloride (0.266 ml, 4.58 mmol) was then added, followed by a drop of dry DMF under argon. After 16 h, the reaction mixture was evaporated under reduced pressure and dried in vacuo. The resultant yellow solid was then redissolved in dichloromethane (50 ml) and added dropwise to a stirred solution of 4-[(4-amino-2-bromophenylthio)methyl] pyridine (D15) (0.822 g, 2.91 mmol) in dichloromethane (40 ml) containing triethylamine (0.424 ml, 3.05 mmol) under argon. After 6 h the reaction mixture was washed with water (1X), 10% sodium hydroxide (1X), dried (Na$_2$SO$_4$) and evaporated under reduced pressure to give the title compound as a brown solid, which was dried in vacuo (1.51 g, 91%).

$^1$H NMR (250 MHz, CDCl$_3$) δ (ppm): 8.51 (d, 2H), 8.10 (m, 2H), 7.97 (m, 4H), 7.48 (m, 3H), 7.32 (d, 1H), 7.18 (m, 3H), 4.05 (s, 2H), 2.70 (s, 3H), 2.35 (s, 3H).

DESCRIPTION 17

N-[3-Bromo-4-(1,2,3,6-tetrahydropyrid-4-ylmethylthio)phenyl]-2'-methyl-4'-(5-methyl-1,2,4-oxadiazol-3-yl)biphenyl-4-carboxamide A stirred solution of N-[3-bromo-4-(pyrid-4-ylmethylthio)phenyl]-2'-methyl-4'-(5-methyl-1,2,4-oxadiazol-3-yl)biphenyl-4-carboxamide (D 16) (1.41 g, 2.46 mmol) in dry DMF (15 ml) was treated with methyl iodide (0.184 ml, 2.95 mmol). After 60 h, the reaction mixture was evaporated under reduced pressure and the residue was triturated with ethyl acetate. The resultant brown solid was filtered off and dried in vacuo. It was redissolved in a mixture of ethanol (150 ml) and water (75 ml), cooled to 0° C. and treated with sodium borohydride (0.165 g, 4.35 mmol) slowly with stirring. After 1 h, the reaction mixture was treated with potassium carbonate solution (50 ml). The resultant suspension was extracted with dichloromethane (3×100 ml) and the combined organic layers were dried (Na$_2$SO$_4$) and evaporated under reduced pressure to give a brown solid, which was purified by silica gel chromatography (10% MeOH/CH$_2$Cl$_2$ as eluant) to give the title compound as a yellow oil (0.680 g, 47%).

$^1$H NMR (250 MHz, CDCl$_3$) δ (ppm): 7.97 (m, 6H) 7.58 (dd, 1H), 7.48 (d, 2H), 7.32 (dd, 2H), 5.51 (s, 1H), 3.50 (s, 2H), 3.00 (s, 2H), 2.70 (s, 3H), 2.62 (m, 3H), 2.40 (s, 3H), 2.35 (m, 1H), 2.30 (s, 3H).

DESCRIPTION 18

Dimethyl 4-cyano-4-(2-fluorophenyl)heptanedioate

2-Fluorophenylacetonitrile (39.85 g, 0.29 mol) and ethyl acrylate (96 ml, 0.89 mol) were stirred at reflux in t-butanol (400 ml) as benzyltrimethylammonium hydroxide (40% solution in MeOH, 140 ml, 0.30 mol) was added portionwise over 48 h. The mixture was then evaporated to dryness, dissolved in ethyl acetate (1000 ml), washed with dilute HCl and brine, dried (Na$_2$SO$_4$) and evaporated to give an oil. This was dissolved in MeOH (300 ml), and a solution of methanolic HCl (formed by cautious addition of thionyl chloride (20 ml) to MeOH (200 ml)) was added. The solution was stirred at reflux for 2 h, evaporated, dissolved in ether, filtered, and evaporated again to yield the title compound (97.6 g, quantitative) as an amber oil.

NMR (200 MHz, CDCl$_3$) δ (ppm): 7.55 (td, 1H), 7.35 (m, 1H), 7.19 (td, 1H), 7.09 (m, 1H), 3.62 (s, 6H), 2.1–2.7 (m, 8H).

DESCRIPTION 19

Methyl 5-cyano-5-(2-fluorophenyl)-2-oxocyclohexane-1-carboxylate

Dimethyl 4-cyano-4-(2-fluorophenyl)heptanedioate (D18, 35.86 g, 0.12 mol) was stirred under Ar in toluene (500 ml) as sodium hydride (80% in mineral oil, 3.5 g, 0.12 mol) was added. Methanol (10 ml) was added dropwise, and the mixture was then stirred at reflux for 16 h, partitioned between ethyl acetate and dilute HCl, and separated. The organic portion was washed with brine, dried ($Na_2SO_4$) and evaporated to an oil. This was dissolved in dichloromethane (500 ml), filtered, and evaporated to give the title compound (30.66 g, 95%) as a cream solid.

NMR (250 MHz, $CDCl_3$) (predominantly enol form) δ (ppm): 12.27 (s, 1H), 7.1–7.6 (m, 4H), 3.80 (s, 3H), 3.09 (d, 1H), 2.85 (m, 2H), 2.2–2.7 (m, 3H).

DESCRIPTION 20

1-(2-Fluorophenyl)-4-oxocyclohexane-1-carboxylic acid

Methyl 5-cyano-5-(2-fluorophenyl)-2-oxocyclohexane-1-carboxylate (D19, 30.66 g, 0.11 mol) was stirred at reflux in c. HCl (500 ml) for 17 h, cooled, diluted with water (500 ml), and extracted with ethyl acetate. This organic portion was extracted with potassium carbonate solution, dried ($Na_2SO_4$) and evaporated to give 4-cyano-4-(2-fluorophenyl)cyclohexanone (9.58 g, 38%) as a yellow foam. The alkaline extract was re-acidified with c. HCl, and the product isolated by extraction with ethyl acetate, drying ($Na_2SO_4$) and evaporation. This gave the title compound (16.36 g, 62%) as a colourless gum.

NMR (200 MHz, $CDCl_3$) δ (ppm): 7.0–7.4 (m, 4H), 2.55–2.9 (m, 4H), 2.2–2.55 (m, 4H).

DESCRIPTION 21

1'-(2-Fluorophenyl)spiro[[1,3]dioxolane-2,4'-cyclohexane]-1'-carboxylic acid 1-(2-Fluorophenyl)-4-oxocyclohexane-1-carboxylic acid (D20, 16.36 g, 69 mmol) was stirred with toluene-4-sulphonic acid hydrate (0.50 g, 3 mmol) and 1,2-ethanediol (35 ml) at reflux in toluene (500 ml), removing the immiscible 1,2-ethanediol/water distillate via a Dean-Stark trap until the distillate was homogenous. The solution was then evaporated, dissolved in ethyl acetate, washed with water and brine, dried ($Na_2SO_4$) and evaporated to give the title compound (19.94 g, quantitative) as an amber syrup, contaminated with some unidentified materials (NMR).

NMR (250 MHz, $CDCl_3$) δ (ppm): 7.1–7.4 (m, 4H), 3.98 (m, 4H), 2.0–2.8 (m, 8H).

DESCRIPTION 22

4'-(2-Fluorophenyl)-4'-(hydroxymethyl)spiro[[1,3]dioxolane-2,1'-cyclohexane]

1'-(2-Fluorophenyl)spiro[[1,3]dioxolane-2,4'-cyclohexane]-1'-carboxylic acid (D21, 19.90 g, 71 mmol) was stirred in THF (500 ml) under Ar as $LiAlH_4$ (5.4 g, 0.14 mol) was added portionwise. The mixture was stirred at reflux for 3 h, cooled and treated successively with water (5.4 ml), 10% NaOH (5.4 ml) and water (16.2 ml). The solids were filtered off, and washed well with ethyl acetate. The combined organics were evaporated to an oil, and purified by chromatography on silica gel, eluting with 50% ethyl acetate/petroleum ether (b.p. 60–80° C.). This gave the title compound (5.44 g, 28%) as a colourless oil.

NMR (250 MHz, $CDCl_3$) δ (ppm): 7.0–7.4 (m, 4H), 3.93 (m, 4H), 3.72 (s, 2H), 2.41 (bd, 2H), 1.5–1.9 (m, 6H).

DESCRIPTION 23

Dispiro[benzofuran-3(2H),1'-cyclohexane-4',2"-[1,3]dioxolane]

Sodium hydride (80% in mineral oil, 1.53 g, 51 mmol) was stirred in dry DMF (30 ml) as 4'-(2-fluorophenyl)-4'-(hydroxymethyl)spiro[[1,3]-dioxolane-2,1'-cyclohexane] (D22, 5.44 g, 20 mmol) was added in dry DMF (70 ml). The mixture was stirred under Ar at 110° C. for 6 h, cooled, diluted with ethyl acetate (500 ml), washed with water and brine, dried ($Na_2SO_4$) and evaporated to give the title compound (4.83 g, 96%) as a straw-coloured solid.

NMR (250 MHz, $CDCl_3$) δ (ppm): 7.15 (m, 2H), 6.88 (t, 1H), 6.79 (d, 1H), 4.39 (s, 2H), 4.00 (s, 4H), 1.6–2.1 (m, 8H).

DESCRIPTION 24

Spiro[benzofuran-3(2H),1'-cyclohexan-4'-one]

Dispiro[benzofuran-3(2H),1'-cyclohexane-4',2"-[1,3]dioxolane] (D23, 1.77 g, 7.2 mmol) was stirred at reflux in a mixture of THF (100 ml) and 5M HCl (25 ml) for 2 h, cooled, diluted with ethyl acetate (150 ml), washed with water and brine, dried ($Na_2SO_4$) and evaporated to give the title compound (1.41 g, 96%) as a yellow solid.

NMR (250 MHz, $CDCl_3$) δ (ppm): 7.15 (m, 2H), 6.93 (t, 1H), 6.86 (d, 1H), 4.57 (s, 2H), 2.5 (m, 4H), 2.2 (m, 4H).

DESCRIPTION 25

1,2,3,5,6,7-Hexahydro-7-oxospiro[4H-azepine-4,3'(2H)-benzofuran]

Spiro[benzofuran-3(2H),1'-cyclohexan-4'-one](D24, 0.91 g, 4.5 mmol), hydroxylamine hydrochloride (0.94 g, 13.5 mmol) and sodium acetate trihydrate (3.6 g, 26 mmol) were stirred at reflux in a mixture of ethanol (40 ml) and water (10 ml) for 1 h, cooled, evaporated to remove ethanol, and diluted with water (50 ml). The light yellow precipitated oxime (0.95 g, 97%) was collected, washed with water, and dried. A portion of this (0.47 g, 2.2 mmol) was stirred in polyphosphoric acid (15 g) at 120° C. for 10 min. The mixture was cooled, dispersed in water (50 ml), and extracted with dichloromethane. The extract was dried ($Na_2SO_4$) and evaporated to give the title compound (0.46 g, 96%) as a cream solid.

NMR (250 MHz, $CDCl_3$) δ (ppm): 7.15 (m, 2H), 6.91 (t, 1H), 6.83 (d, 1H), 6.38 (b s, 1H), 4.42 (ABq, 2H), 3.33 (m, 2H), 2.54 (m, 2H), 1.8–2.1 (m, 4H)

DESCRIPTION 26

1,2,3,5,6,7-Hexahydro-1-methyl-7-oxospiro[4H-azepine-4,3'(2H)-benzofuran]

1,2,3,5,6,7-Hexahydro-7-oxospiro[4H-azepine-4,3'(2H)-benzofuran] (D25, 0.42 g, 1.9 mmol) was dissolved in dry DMF (10 ml) and added under Ar to sodium hydride (80% in mineral oil, 0.09 g, 3 mmol) in dry DMF (1 ml). After stirring for 5 min, iodomethane (0.24 ml, 3.8 mmol) was added. The mixture was stirred for 1 h, diluted with ethyl acetate (150 ml), washed with water and brine, dried ($Na_2SO_4$) and evaporated to give the title compound (0.36 g, 79%) as yellow semi-solid.

NMR (250 MHz, $CDCl_3$) δ (ppm): 7.18 (t, 1H), 7.10 (d, 1H), 6.90 (t, 1H), 6.83 (d, 1H), 4.40 (s, 2H), 3.65 (m, 1H), 3.30 (m, 1H), 3.07 (s, 3H), 2.60 (m, 2H), 1.95 (m, 4H).

DESCRIPTION 27

1,2,3,5,6,7-Hexahydro-1-methyl-5'-nitro-7-oxospiro[4H-azepine-4,3'(2H)-benzofuran]

This material was prepared from 1,2,3,5,6,7-hexahydro-1-methyl-7-oxospiro[4H-azepine-4,3'(2H)-benzofuran]

(D26, 0.36 g, 1.5 mmol) following the procedure of Description 5, but with a reaction time of 4 h. This gave the title compound (0.41 g, 97%) as a yellow solid, containing ca. 20% of the corresponding 7'-nitro isomer (NMR).

NMR (250 MHz, CDCl$_3$) δ (ppm): 8.15 (dd, 1H), 8.02 (d, 1H), 6.87 (d, 1H), 4.58 (s, 2H), 3.65 (m, 1H), 3.30 (m, 1H), 3.08 (s, 3H), 2.53 (m, 2H), 2.0 (m, 4H).

DESCRIPTION 28

5'-Amino-1,2,3,5,6,7-hexahydro-1-methyl-7-oxospiro[4H-azepine-4,3'(2H)-benzofuran]

This material was prepared from 1,2,3,5,6,7-hexahydro-1-methyl-5'-nitro-7-oxospiro[4H-azepine-4,3'(2H)-benzofuran] (D27, 0.68 g, 2.5 mmol) following the procedure of DESCRIPTION 6, but using acetic acid as solvent. This gave the title compound (0.19 g, 31%) as a white solid.

NMR (250 MHz, CD$_3$OD/CDCl$_3$) δ (ppm): 6.60 (m, 3H), 4.36 (ABq, 2H), 3.70 (m, 1H), 3.35 (m, 1H), 3.06 (s, 3H), 2.5–2.7 (m, 2H), 1.90 (m, 4H).

DESCRIPTION 29

5'-Amino-1,2,3,5,6,7-hexahydro-1-methylspiro[4H-azepine-4,3'(2H)-benzofuran]

This material was prepared from 5'-amino-1,2,3,5,6,7-hexahydro-1-methyl-7-oxospiro[4H-azepine-4,3'(2H)-benzofuran] (D28, 0.19 g, 0.8 mmol), following the procedure of Description 22, but washing the aluminium salts with 20% methanol in dichloromethane. This gave dark green crude material (0.24 g), used without purification.

EXAMPLE 1

N-(2,3-Dihydro-1'-methylspiro[4H-benzopyran-6-yl-4,4'-piperidine])-2'-methyl-4'-(5-methyl-1,2,4-oxadiazol-3-yl)biphenyl-4-carboxamide A suspension of 2'-methyl-4'-(5-methyl-1,2,4-oxadiazol-3-yl)biphenyl-4-carboxylic acid (EP 0533268A1) (250 mg, 0.86 mmole) in thionyl chloride (6 ml) was heated under reflux for 2 h, then concentrated in vacuo to leave the acid chloride as a yellow solid. This was dissolved in dichloromethane (10 ml) and added to a stirred solution of 6-amino-2,3-dihydro-1'-methylspiro[4H-benzopyran-4,4'-piperidine] (D7, 200 mg, 0.86 mmole) and triethylamine (0.22 ml, 1.6 mmole) in dichloromethane (20 ml). The reaction mixture was stirred at room temp. for 20 h, then treated with 10% Na$_2$CO$_3$ solution (30 ml) and extracted with dichloromethane (2×50 ml). The combined extract was dried (Na$_2$SO$_4$), concentrated in vacuo and the residue chromatographed on silica gel eluting with 3% methanol/chloroform to afford the title compound (205 mg, 47%). The oxalate salt crystallised from acetone/ether mp. 143–145° C.

$^1$H NMR (free base) (200 MHz, CDCl$_3$)

δ(ppm): 8.02–7.87 (m, 5H), 7.58 (d, 1H), 7.49–7.38 (m, 3H), 7.33 (d, 1H), 6.82 (d, 1H), 4.18–4.07 (m, 2H), 2.72 (br t, 2H), 2.67 (s, 3H), 2.33 (s, 6H), 2.30–2.15 (m, 4H), 2.05–1.95 (m, 2H), 1.70–1.57 (m, 2H).

EXAMPLE 2

N-(2,3-Dihydrospiro[4H-benzopyran-6-yl-4,4'-piperidine])-2'-methyl-4'-(5-methyl-1,2,4-oxadiazol-3-yl)biphenyl-4-carboxamide A solution of N-(2,3-dihydro-1'-ethoxycarbonylspiro[4H-benzopyran-6-yl-4,4'-piperidine])-2'-methyl-4'-(5-methyl-1,2,4-oxadiazol-3-yl)biphenyl-4-carboxamide (D8, 100 mg, 0.18 mmole) in methanol (25 ml), THF (20 ml) and 10% NaOH solution (25 ml) was stirred at room temp. for 5 days, then concentrated in vacuo. The residue was acidified with 5M HCl acid, washed with ethyl acetate, then basified with K$_2$CO$_3$ and extracted with ethyl acetate (2×50 ml). The combined extract was dried (Na$_2$SO$_4$), concentrated in vacuo and the residue purified by preparative TLC on a silica gel plate eluting wtih 20% methanol/chloroform to afford the title compound as a white solid (30 mg, 34%) mp 218–220° C.

$^1$H NMR (200 MHz, CDCl$_3$)

δ(ppm): 8.30 (s, 1H), 8.04–7.90 (m, 4H), 7.73 (d, 1H), 7.48–7.27 (m, 4H), 6.80 (d, 1H), 4.17–4.06 (m, 2H), 3.08–2.80 (m, 4H), 2.68 (s, 3H), 2.32 (s, 3H), 2.15–1.95 (m, 4H), 1.70–1.55 (m, 2H).

EXAMPLE 3

N-(2,3-Dihydro-1'-methylspiro[benzofuran-5-yl-3,4'-piperidine])-2'-methyl-4'-(5-methyl-1,2,4-oxadiazol-3-yl)biphenyl-4-carboxamide The title compound was prepared from 5-amino-2,3-dihydro-1'-methylspiro[benzofuran-3,4'-piperidine] (D13), using a procedure similar to that of Example 1, in 80% yield. The oxalate salt crystallised from acetone, m.p. 170° C. (decomp.).

$^1$H NMR (oxalate salt) (200 MHz, d$^6$DMSO) δ(ppm): 10.31 (s, 1H), 8.15–7.9 (m, 4H), 7.7–7.55 (m, 4H), 7.45 (d, 1H), 6.83 (d, 1H), 4.50 (s, 2H), 3.41 (d, 2H), 3.02 (t, 2H), 2.75 (s, 3H), 2.70 (s, 3H), 2.37 (s, 3H), 2.2–1.85 (m, 4H).

EXAMPLE 4

N-(2,3-Dihydro-1'-methylspiro[benzothiophen-5-yl-3,4'-piperidine])-2'-methyl-4'-(5-methyl-1,2,4-oxadiazol-5-yl)biphenyl-4-carboxamide A solution of tributyltin hydride (0.273 ml, 1.018 mmol) in benzene (10 ml) was added dropwise over 30 minutes to a stirred solution of N-[3-bromo-4-(1,2,3,6-tetrahydropyrid-4-ylmethylthio)phenyl]-2'-methyl-4'-(5-methyl-1,2,4-oxadiazol-3-yl)biphenyl-4-carboxamide (D17) (0.300 g, 0.509 mmol) in benzene (15 ml), containing AIBN (4 mg) under argon at reflux. Reflux was continued for a further 4 h, after which the reaction mixture was allowed to cool and evaporated under reduced pressure to give a brown oil. The oil was purified by prep. TLC (10% MeOH/CH$_2$Cl$_2$ as eluant) to give the title compound as a cream foam (0.069 g, 27%), which was subsequently converted to its oxalate salt. m.pt. 170–174° C.

$^1$H NMR (oxalate salt) (270 MHz, d$^6$DMSO) δ (ppm): 10.40 (s, 1H), 8.05 (d, 2H), 8.01 (s, 1H), 7.92 (d, 1H), 7.80 (s, 1H), 7.58 (m, 3H), 7.47 (d, 1H), 7.23 (d, 1H), 3.51 (s, 2H), 3.42 (m, 2H), 3.13 (m, 2H), 2.80 (s, 3H), 2.70 (s, 3H), 2.38 (s, 3H), 2.00 (m, 4H).

EXAMPLE 5

N-(1,2,3,5,6,7-Hexahydro-1-methylspiro[4H-azepine-4,3'(2H)-benzofuran-5'-yl])-2'-methyl-4 '-(5-methyl-1,2,4-oxadiazol-3-yl)biphenyl-4-carboxamide This material was prepared from 5'-amino-1,2,3,5,6,7-hexahydro-1-methylspiro[4H-azepine-4,3'(2H)-benzofuran] (D29, 0.24 g), following the procedure of Example 1. The oxalate salt precipitated from acetone/ether as a cream powder (0.078 g, 16%).

$^1$H NMR (oxalate salt) (200 MHz, d$^6$DMSO) δ (ppm): 10.28 (s, 1H), 8.07 (d, 2H), 7.8–8.0 (m, 3H), 7.57 (d, 2H), 7.46 (d, 2H) 6.80 (d, 1H), 4.32 (s, 2H), 3.2–3.5 (m, 4H), 2.82 (s, 3H), 2.70 (s, 3H), 2.36 (s, 3H), 1.8–2.3 (m, 6H).

We claim:

1. A compound of formula (I) or a salt thereof:

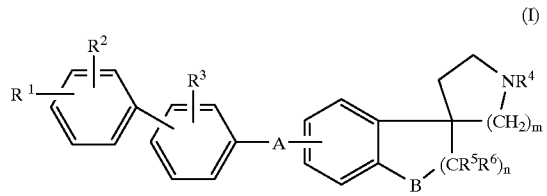

in which

R$^1$ is oxadiazole;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl;

R$^4$ is hydrogen or C$_{1-6}$alkyl;

R$^5$ and R$^6$ are independently hydrogen or C$_{1-6}$alkyl;

A is CONH;

B is oxygen, sulphur, CR$^{12}$R$^{13}$ or NR$^{14}$ where R$^{12}$, R$^{13}$ and R$^{14}$ are independently hydrogen or C$_{1-6}$alkyl;

m is 1, 2 or 3; and n is 1, 2 or 3.

2. A compound according to claim 1 in which R$^2$ is C$_{1-6}$alkyl.

3. A compound according to claim 1 in which R$^3$ is hydrogen.

4. A compound according to claim 1 in which n is 1 and m is 2.

5. A compound according to claim 1 which is:

N-(2,3-Dihydro-1'-methylspiro[4H-benzopyran-6-yl-4,4'-piperidine])-2'-methyl-4'-(5-methyl-1,2,4-oxadiazol-3-yl)biphenyl-4-carboxamide, N-(2,3-Dihydrospiro[4H-benzopyran-6-yl-4,4'-piperidine])-2'-methyl-4'-(5-methyl-1,2,4-oxadiazol-3-yl)biphenyl-4-carboxamide, N-(2,3-Dihydro-1-methylspiro[benzofuran-5-yl-3,4'-piperidine])-2'-methyl-4'-(5-methyl-1,2,4-oxadiazol-3-yl)biphenyl-4-carboxamide, N-(2,3-Dihydro-1'-methylspiro[benzothiophen-5-yl-3,4'-piperidine])-2'-methyl-4'-(5-methyl-1,2,4-oxadiazol-5-yl)biphenyl-4-carboxamide, N-(1,2,3,5,6,7-Hexahydro-1-methylspiro[4H-azepine-4,3'(2H)-benzofuran-5'-yl])-2'-methyl-4'-(5-methyl-1,2,4-oxadiazol-3-yl)biphenyl-4-carboxamide, or pharmaceutically acceptable salts thereof.

6. A pharmaceutical composition which comprises a compound of claim 1 in association with a pharmaceutically acceptable carrier or excipient.

7. A method of treating depression, anxiety, which method involves treating a patient in need thereof with a therapeutically effective amount of a compound of formula (I) as described in claim 1.

8. A process for the preparation of a compound of formula (I), as defined in claim 1, which comprises:

coupling a compound of formula (II):

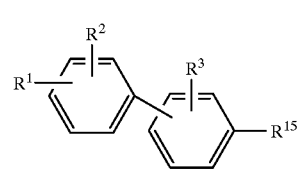

with a compound of formula (III):

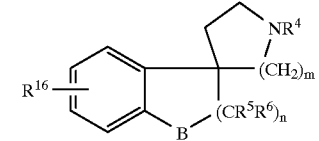

wherein R$^1$, R$^2$, R$^3$, R$^4$, R$^5$, R$^6$, B, m and n are as defined in formula (I), as defined in claim 1, and R$^{15}$ and R$^{16}$ are functional groups which when coupled form the —CONH— linkage;

and then optionally forming a pharmaceutically acceptable salt.

* * * * *